(12) United States Patent
Stein et al.

(10) Patent No.: US 7,297,535 B2
(45) Date of Patent: Nov. 20, 2007

(54) USE OF THE HUMAN LRP/MVP PROMOTOR FOR A VECTOR THAT CAN BE INDUCED BY THERAPY

(75) Inventors: Ulrike Stein, Schwanebeck (DE); Christian Lange, Berlin (DE); Wolfgang Walther, Schwanebeck (DE); Peter Michael Schlag, Berlin (DE)

(73) Assignee: Max-Delbrück-Centrum Für Molekulare Medizin, Berlin (DE)

( * ) Notice: Subject to any disclaimer, the term of this patent is extended or adjusted under 35 U.S.C. 154(b) by 529 days.

(21) Appl. No.: 10/416,209

(22) PCT Filed: Nov. 8, 2001

(86) PCT No.: PCT/DE01/04151

§ 371 (c)(1), (2), (4) Date: Aug. 8, 2003

(87) PCT Pub. No.: WO02/38188

PCT Pub. Date: May 16, 2002

(65) Prior Publication Data

US 2004/0053879 A1    Mar. 18, 2004

(30) Foreign Application Priority Data

Nov. 8, 2000    (DE) .................... 100 55 383

(51) Int. Cl.
C12N 15/85 (2006.01)
C07H 21/04 (2006.01)

(52) U.S. Cl. .................... 435/320.1; 536/24.1; 514/44

(58) Field of Classification Search .................... None
See application file for complete search history.

(56) References Cited

U.S. PATENT DOCUMENTS 5,968,735 A    10/1999    Stein et al.

FOREIGN PATENT DOCUMENTS

EP    0 657 539 A    6/1995

OTHER PUBLICATIONS

Pietrzkowski et al. (1991)) Exp. Cell Res. 193:283-290.*
Chan et al. (2001) Plant Mol. Biol. 46 :131-141.*
Omilli et al. (1986) Mol. Cell Biol. 6:1875-1885.*
Arnone et al. (1997) Development 124:1851-1864.*
Verma et al. (1997) Nature 389:239-242.*
Marshall (1995) Science 269:1050-1055.*
Orkin et al. (1995) Report and recommendations of the panel to assess the NIH investment in research on gene therapy, available at http://www.nih.gov/news/panelrep.html.*
Eck et al. (1996) Goodman & Gilman's The Pharmacological Basis of Therapeutics, 9th Edition, Chapter 5, McGraw-Hill, NY.*
Ross et al. (1996) Human gene Therapy 7:1781-1790.*
Rubanyi (2001) Mol. Aspects Med. 22:113-142.*
Gomez-Navarro et al. (2002) From: Mol. Basis Hum. Cancer (W.B. Coleman and G.J. Tsongalis, eds.), Humana Press Inc., Totowa, NJ, pp. 541-556.*
Gottesman (2002) Cancer Gene Ther. 10:501-508.*
C. Lange, Biochemical and Biophysical Research Communications, 278, 125-133 (2000) ; XP-002208365.
Doe Joint Genome Inst., "Sequencing of Human Chromosome 16", XP-002208366, EMBL Accession No.: AC009133; Jul. 5, 2002.
U. Stein, "*Homo sapiens* MVP Gene, Promoter Region", EMBL Accession No.: AJ238509, Dec. 1, 2000; XP-0022083667.
G. Scheffer et al., Nature Medicine, vol. 1, No. 6, Jun. 1995, pp. 578-582, XP-002002543.
W. Walther et al., Molecular Biotechnology, vol. 6, 1996, pp. 267-286.
W. Walther et al., Drugs, Aug. 2000, 60 (2), pp. 249-271.
S. Li et al., Gene Therapy (2000) 7, pp. 31-34.

* cited by examiner

*Primary Examiner*—Daniel M. Sullivan
(74) *Attorney, Agent, or Firm*—Buchanan Ingersoll & Rooney PC

(57) ABSTRACT

Embodiments of the invention relate to a vector system that allows one to induce expression of therapeutically relevant genes in mammalian cells. Such a vector system may be useful for medicine and in the pharmaceutical industry. A vector comprises base structures suitable for expression in mammalian cells as well as either the whole of or parts of the gene promoter of human Major Vault Protein (MVP), also known as LRP (Lung Resistance Protein) as well as a gene encoding a therapeutic protein or non-translated RNA. As the MVP promoter is inducible by therapy (for example, but not limited to, chemotherapy or hyperthermia), the vector system provides combinations of therapeutic methods with gene therapy in a controlled fashion, resulting in more efficient treatment of tumor diseases.

7 Claims, 2 Drawing Sheets

USE OF THE HUMAN LRP/MVP PROMOTOR FOR A VECTOR THAT CAN BE INDUCED BY THERAPY

Figure 1:
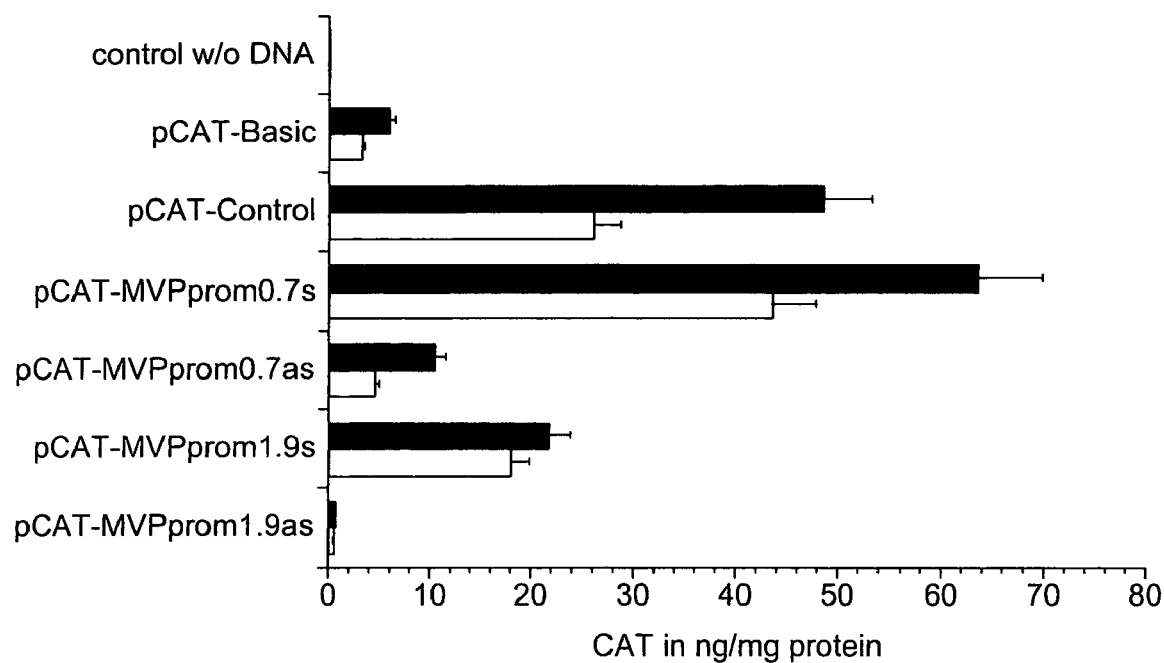

This application is the national phase under 35 U.S.C. §371 of PCT International Application No. PCT/DE01/04151 which has an International filing date of Nov. 8, 2001, which designated the United States of America.

SUBJECT MATTER OF THE INVENTION

The subject matter of the invention is a therapy-regulatable vector system of the gene promoter of the human lung resistance protein (LRP/MVP). This vector system for the therapy-inducible expression of therapeutically relevant genes in mammalian cells is to be used in the pharmaceutical industry and in medicine.

SCIENTIFIC BACKGROUND AND DESCRIPTION OF INVENTION

Increasing, gene-therapy strategies are pursued for the treatment of tumor diseases. It is hereby often of interest to express the therapeutic gene for a defined period of time in a sufficient quantity in the target cells and let it become effective for tumor therapy. For this reason, promoters that are inducible by way of defined, therapy-associated modalities, are important for the construction of conditionally active vectors in gene therapy. Vectors that can be regulated by a specific therapy enable a controlled expression of the therapeutic gene (Walther 1996, Mol. Biotechnol. 6: 267-86).

The invention has the objective of regulating the tumor gene therapy through therapeutic modalities, such as chemotherapy or hyperthermia, for the period of these therapies, so that the gene therapy, together with chemotherapy, hyperthermia, and other means, results in a controlled, more efficient treatment of the tumor disease.

The objective of the invention is realized by using an expression vector according to claim 1. Secondary claims characterize the vector according to the invention in more detail. An essential characteristic is a vector that is characterized by a therapy-inducible LRP/MVP promoter or a defined sequence thereof and by a gene encoding for a therapeutically relevant protein. This promoter is inducible by chemotherapy, hyperthermia, and other means, and in this way permits the therapy-induced expression of subsequent therapeutic genes. Therapeutically relevant proteins include cytokines, enzymes, antibodies, apoptosis genes, resistance genes. anti-oncogenes, tumor necrosis factor alpha, interferon alpha, interferon gamma, interleukin 2, interleukin 6, interleukin 7, interleukin 12, GM-CSF, G-CSF, herpes simplex thymidine kinase. cytosine deaminase, nitroreductase, and cytochrome P-450.

It was unexpectedly found that the human LRP/MVP gene promoter isolated and cloned by the inventors is inducible through therapy-relevant factors, and the expression of subsequent genes thus can be controlled. These inductors include chemotherapy agents, such as cisplatin, 5-fluoruracil, adriamycin, vincristin etc., but also other therapy-associated factors, such as, for example, hyperthermia and irradiation. The vector of the invention according to Claim 1 therefore enables the cytostatic- and/or hyperthermia-induced expression of therapeutic genes in the target cells (tumor cells), and therefore a combination of gene therapy and chemotherapy, hyperthermia, and/or irradiation.

As a base structure for the vectors according to the invention, all constructs suitable for expression in mammalian cells can be used. These include vector base structures based on DNA (for example, adenoviruses, AAV) or RNA viral vectors (for example, MoMuLV, HIV). The vectors according to the invention therefore can be introduced into the target cells with suitable non-viral (gene gun, liposomes, electroporation) or viral carrier systems and unfold the therapeutic effect. The therapeutic effect of the vector according to the invention is created in that, after the vector transfer by chemotherapy, hyperthermia, or irradiation, the expression of the therapeutic gene is induced by the LRP/MVP promoter, and the resulting antitumor gene products are released in the tumor cell and, as the case may be, in its environment. With the help of the invention, the combination of gene therapy (antitumor effects of the induced therapeutic genes) and chemotherapy, hyperthermia, and/or irradiation is able to result in improved tumor therapy.

The invention is described in more detail using the following embodiments:

EXEMPLARY EMBODIMENT 1

Cloning of Human LRP/MVP Gene Promoter

Isolation of the Human LRP/MVP Promoter

From the human, multidrug-resistant, but non-P-glycoprotein-expressing lung cancer cell line SW1573, we isolated a 5' upstream sequence of the LRP gene with a size of approximately 1.9 kb (Claim 1). For this, the genomic DNA was isolated from SW1573 cells, and the genome walking method was used in different PCR versions. After cloning the approximately 1.9 kb 5' flanking sequence of the LRP gene, several consensus elements for the binding of transcription factors were identified after the sequence analysis: for example, an inverted CCMT box (Y-box) for binding the transcription factor YB-1 described in the context with resistance, an E-box for binding c-myc, as well as sequences for binding p53 and SP1.

Identification of the Transcription Start

To identify the transcription start, we constructed a cDNA library of the SW1573 cell line using RACE-PCR (rapid amplification of cDNA ends). We hereby found an alternative 3' splicing site in intron 1 of the LRP gene. This alternative splicing within the 5' untranslated region in intron 1 then results in two different versions of LRP-mRNA.

Detection of Promoter Activity

To analyze the promoter activity, the following constructs were produced and tested with a chloramphenicol acetyl transferase (CAT) assay: pCAT-MVPprom1.9s (includes the 1.9 kb sequence in sense orientation under control of the CAT promoter), pCAT-MVPprom1.9 as (in antisense orientation), pCAT-MVPprom0.7s (includes a 0.7 kb deletion version of the 1.9 kb sequence), and pCAT-MVPprom0.7 as. The pCAT basic (without promoter) and pCAT control constructs (with SV40 promoter) as well as the mentioned LRP promoter each were transfected into two human tumor cell lines, and a reporter gene assay (CAT-ELISA) was performed. Promoter activities were detected for both LRP promoter constructs, whereby the one for pCAT-MVPprom0.7s was unexpectedly higher than the one for pCAT-MVPprom1.9s and pCAT control (FIG. 1).

Detection of Inducibility via Cytostatics

Figure 2:
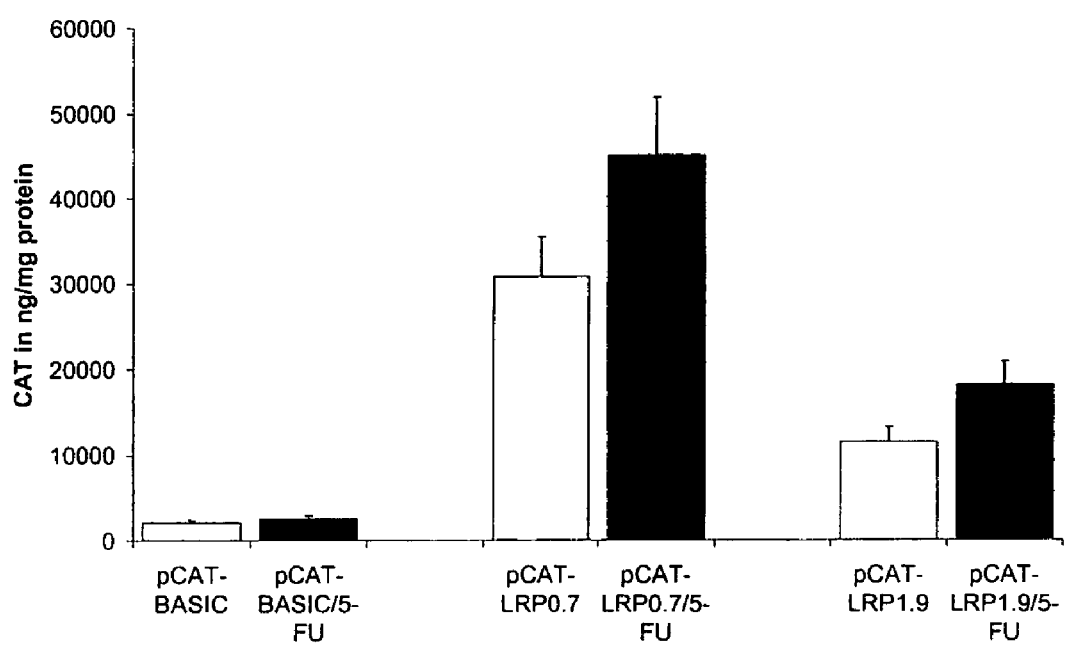

Beyond the basal promoter activity, the LRP/MVP-promoter-mediated expression of subsequent genes can be induced via a number of cytostatics. Below, the 5-fluoruracil-induced CAT expression is shown as an example: (FIG. 2)

EXEMPLARY EMBODIMENT 2

Construction of the Therapy-Inducible Vector Construct Using the LRP/MVP Gene Promoter Constructions of Therapy-Inducible Vectors for Expressing Therapeutic Genes The LRP/MVP promoter or parts thereof are inserted into vector base structures in such a way that the promoter regulates the expression of a subsequent therapeutic gene. Such vector base structures may be non-viral expression vectors (for example, pcDNA3, pcDNA6, etc.) or viral vector base structures (for example, adenoviral vectors, retroviral vectors pLXSN, pLXIN, etc.).

Gene Transfer of Vector Constructs

The transfer of the vector constructs may take place with the help of non-viral transfer technologies. Such technologies may be the vector injection, in vivo electroporation, particle bombardment, needle injection, or liposomal transfer (Li, 2000, Gene Ther. 7: 31-4). Alternatively, for viral vector constructs, viral gene transfer can be used for the transfer into the target cells by way of producing recombinant DNA or RNA virus particles with the help of suitable helper cell lines (Walther, 2000, Drugs 60: 249-71). These technologies are already being used clinically or are used prospectively for treating cancer patients.

LEGENDS FOR FIGURES

FIG. 1

Detection of LRP/MVP promoter activity in CAT assay in human colon cancer cell lines HCT116 (black) and HCT15 (white).

FIG. 2

Detection of inducibility of LRP/MVP promoter by 5-fluoruracil (black) 24 h after cytostatic administration.

The invention claimed is:

1. An expression vector comprising: a vector base structure that is suitable for expression in mammalian cells, and a first nucleotide sequence encoding at least one therapeutic protein or nontranslated ribonucleic acid (RNA), and a second nucleotide sequence consisting of the nucleotide sequence of SEQ ID NO: 1.

2. The expression vector according to claim 1, wherein said therapeutic protein is selected from the group consisting of a cytokine, enzyme, antibody, apoptosis gene, and antioncogene.

3. The expression vector according to claim 1, wherein the therapeutic protein is selected from the group consisting of tumor necrosis factor alpha, interferon alpha, interferon gamma, interleukin 2, interleukin 6, interleukin 7, interleukin 12, GM-CSF and G-CSF.

4. The expression vector of claim 1, wherein the therapeutic protein is selected from the group consisting of herpes simplex thymidine kinase, cytosine deaminase, nitroreductase, and cytochrome P-450.

5. The expression vector of claim 1, wherein the expression vector is suitable for non-viral gene transfer.

6. The expression vector of claim 1, wherein said vector is packaged in viral particles for viral gene transfer.

7. The expression vector of claim 1, wherein said second nucleotide sequence is operably linked to said first nucleotide sequence, and wherein the expression of said first nucleotide sequence increases in response to the cancer chemotherapeutic agent 5-FU.

* * * * *

SEQUENCE LISTING

```
<160> NUMBER OF SEQ ID NOS: 1

<210> SEQ ID NO 1
<211> LENGTH: 1903
<212> TYPE: DNA
<213> ORGANISM: Homo sapiens
<220> FEATURE:
<221> NAME/KEY: promoter
<222> LOCATION: (1)..(1903)
<223> OTHER INFORMATION: human LRP/MVP-Promotor

<400> SEQUENCE: 1
ggtacctgca gtggcatgat cttggctcac tgcaatctcc acctcctggg ttgaagcgat      60
tctcctacct cagtctcctg agtagctggg attacaagga cacgtcacca cgcctagcta     120 attttttgtat tttctagtag agaggggtt tcgccatgtt ggcgaggctg gtcttgaact     180
cctgacctaa agcttcccaa agtgcctgcc tcagcttccc aaagtgctgg aattacaggc     240
gtgagctgct gcactcagcc ataaatcgtg tcacttttcc acttaaaatt ttccaaggga     300
ttccatcttg ccagggaaga gcatgtcaaa ggagaatcca agcgcttttc ccgccacctc     360
cagttctctg cactcttttt tttgttttg tttttggcga gtagggaga cggagtgtag     420 ctgtgtcacc gaggctggag tgcagtagtg cgatcttggc tcattgcaac ctccacctcc     480
cgggttcaag cgattctcct gcctcagcct tccaagtagc tgggattaca ggcgcccacc     540
accacgccca gctaattttt tgtgttggcc aggctggact caaactcctg acctcgagag     600
ttgcccacct cagcctccca aagtgctggc attacaagcg tgaaccacca tgcccggcct     660
gcactcttct ttgaacagaa ctctgttctt gtcctggggc ctatacccctt gccattcccc     720 tgcccagtat gttcctccct gttcttcaca ttacctgtgc cttcctgtca atcaagatct     780
ttgcctctca ccctctctga ggtccaaccc tgaacctcag gtcctccaag acagaggcct     840
ggggacctgc atgtttaacc agctcccccaa gtgatgagtg aggtccaggc aggtatggtg     900
tacaccacct ccatcccttc catgtatctt accttcctct tctccaggaa gctcagcccg     960
gagccagaaa cgggaggccc gcctggacaa ggtgctgtcg gacatgaaga gacacaagaa    1020
```

```
                                  -continued gctggaggag cagatccttc gtaccgggag ggacctcttc agcctggact cggaggaccc       1080
cagccccgcc agcccccac tccgatcctc cgggagtagt ctcttccctc ggcagcggaa        1140
atactgattc ccactgctcc tgcctctagg gtgcagtgtc cgtacctgct ggagcctggg       1200
ccctccttcc ccagcccaga cattgagaaa cttgggaaga agagagaaac ctcaagctcc      1260
caaacagcac gttgcgggaa agaggaagag agagtgtgag tgtgtgtgtg tgtttttct        1320 attgaacacc tgtagagtgt gtgtgtgtgt tttctattga acacctatag agagagtgtg       1380
tgtgttttct attgaacatc tatatagaga gagtgtgtga gtgtgtgttt tctattgaac       1440
acctattcag agacctggac tgaattttct gagtctgaaa taaaagatgc agagctatca      1500
tctcttaaaa ggaggggctg tagctgtagc tcaacagtta ggccccactt gaagggagag      1560
gcagaattgt actcacccag attggaaaat gaaagccaga tgggtagagg tgccctcagt      1620
tagcacctgt cccatctcgg gccctccaac tcctcccagt cccactccag tgcagccagc      1680
tggctccaag gtagaaaccc atgagcactc agggagcagt gtgccttcag ctgcagcaga      1740
agcagcccgg aggataaaat gagaaccagc tgcacacggg ccctttaact cccaagcccc      1800
acccctgggc ttggcctgcc ttgccctgcc gggaagtgat ccccaaggca gggtgagagt      1860
tccccatctg aggcgtttgt tgcagctacc tgcacttcta gat                        1903
```